United States Patent
Johansson et al.

(10) Patent No.: US 10,996,220 B2
(45) Date of Patent: May 4, 2021

(54) METHODS FOR PREPARING A DILUTION SERIES

(71) Applicant: CYTIVA SWEDEN AB, Uppsala (SE)

(72) Inventors: Johan Dan Johansson, Uppsala (SE); Tomas Dalmo, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 305 days.

(21) Appl. No.: 15/938,903

(22) Filed: Mar. 28, 2018

(65) Prior Publication Data

US 2018/0284113 A1 Oct. 4, 2018

(30) Foreign Application Priority Data

Mar. 31, 2017 (GB) .................................. 1705280.4

(51) Int. Cl.
*G01N 33/543* (2006.01)
*G01N 1/38* (2006.01)
(Continued)

(52) U.S. Cl.
CPC ......... *G01N 33/54373* (2013.01); *G01N 1/38* (2013.01); *G01N 21/553* (2013.01);
(Continued)

(58) Field of Classification Search
CPC ....... G01N 21/553; G01N 2035/00702; G01N 33/54373; G01N 1/38; G01N 33/54393;
(Continued)

(56) References Cited

U.S. PATENT DOCUMENTS 5,646,727 A * 7/1997 Hammer ............. F04B 43/1253
356/315
5,783,450 A * 7/1998 Yoshida ................. G01N 30/88
422/70
(Continued)

FOREIGN PATENT DOCUMENTS

EP 1631824 B1 4/2018
FR 2 745 083 A1 8/1997
(Continued)

OTHER PUBLICATIONS

Japanese Office Action received in Application No. 2018-515225 received Jun. 15, 2020, 4 pages.
(Continued)

*Primary Examiner* — Shogo Sasaki
(74) *Attorney, Agent, or Firm* — Jeff B. Vockrodt; Culhane Meadow, PLLC (57) ABSTRACT

Methods for preparing a dilution series for use in forming calibration curves, preferably in the field of surface plasmon resonance, are provided. In one example, a dilution series is prepared by using receptacles such as tubes of a micro well plate in which samples of the dilution series are mixed. In another example, a dilution series is prepared by using a convection mix in a receptacle for achieving a concentration gradient in the sample. A biosensor system arranged to perform steps of methods disclosed are provided. A data processing apparatus and a software for performing steps of methods disclosed, and a computer readable medium for storing the software are also provided.

9 Claims, 10 Drawing Sheets

(51) Int. Cl.
  *G01N 21/552* (2014.01)
  *G01N 33/531* (2006.01)
  *G01N 35/00* (2006.01)
(52) U.S. Cl.
  CPC ..... *G01N 33/531* (2013.01); *G01N 33/54393* (2013.01); *G01N 2001/383* (2013.01); *G01N 2035/00702* (2013.01); *G01N 2201/12746* (2013.01)
(58) Field of Classification Search
  CPC ........... G01N 2001/383; G01N 33/531; G01N 2201/12746
  See application file for complete search history.

(56) References Cited

U.S. PATENT DOCUMENTS

| | | | | |
|---|---|---|---|---|
| 5,928,953 | A * | 7/1999 | Kallback | G01N 35/1097 422/504 |
| 7,998,434 | B2 * | 8/2011 | Shaw | G01N 1/38 422/501 |
| 8,758,703 | B2 * | 6/2014 | Shaw | G01N 1/38 422/501 |
| 9,658,143 | B1 * | 5/2017 | Field | G01N 1/38 |
| 2003/0175760 | A1 | 9/2003 | Walker et al. | |
| 2006/0020119 | A1 | 1/2006 | Grimes et al. | |
| 2008/0254541 | A1 | 10/2008 | Kang et al. | |
| 2012/0264233 | A1 | 10/2012 | Jansson | |
| 2014/0141529 | A1 | 5/2014 | Karlsson et al. | |

FOREIGN PATENT DOCUMENTS

| | | |
|---|---|---|
| JP | 2006322940 A | 11/2006 |
| JP | 2006527365 A | 11/2006 |
| JP | 2007506967 A | 3/2007 |
| JP | 2008500968 A | 1/2008 |
| JP | 2012127807 A | 7/2012 |
| JP | 2013515260 A | 5/2013 |
| JP | 2014521062 A | 8/2014 |
| WO | 2005029077 A1 | 3/2005 |
| WO | 2006/012454 A1 | 2/2006 |
| WO | 2016/066591 A1 | 5/2016 |
| WO | 2016066591 A1 | 5/2016 |
| WO | 2017/011404 A1 | 1/2017 |

OTHER PUBLICATIONS

GB Search Report for corresponding GB application No. GB1705280.4 dated Jan. 26, 2018; 4 pages.
GE Healthcare Bio-Sciences AB; "Biacore (RTM) Assay Handbook", published May 2012; available at http://www.biophysics.bioc.cam.ac.uk/wp-content/uploads/2011/02/Biacore_assay_handbook.pdf; particularly pp. 28-29 and 67-70. 78 pages total.
Extended European Search Report and Opinion issued in connection with corresponding EP Application No. 18163599.6 dated Sep. 3, 2018.

* cited by examiner

METHODS FOR PREPARING A DILUTION SERIES

TECHNICAL FIELD

The present invention relates to methods for preparing dilution series for use in forming calibration curves, preferably for the field of surface plasmon resonance.

BACKGROUND

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by GE Healthcare, which uses surface plasmon resonance (SPR) for detecting interactions between molecules in a sample and molecular structures immobilized on a sensing surface. In the following, the molecules in the sample are referred to as analyte and the molecular structures immobilized on the sensing surface will be denoted as ligand. As sample is passed over the sensing surface, the progress of binding directly reflects the rate at which the interaction occurs through changes in refractive index at the sensing surface that correspond to changes in signal intensity during the binding. Injection of the sample is followed by a buffer flow during which the detector response reflects the rate of dissociation of the complex on the surface. A typical output from the BIACORE® system is a graph or curve describing change in refractive index at the sensing surface and thereby the progress of the molecular interaction with time, including an association phase part and a dissociation phase part. This graph or curve, which is usually displayed on a computer screen, is often referred to as a binding curve or "sensorgram".

With the BIACORE® system (and analogous sensor systems) it is thus possible to determine a plurality of interaction parameters for the molecules used as ligand and analyte. These parameters include kinetic rate constants for binding (association) and dissociation in the molecular interaction as well as the affinity for the interaction on the sensing surface between analyte and ligand. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants.

Several factors may cause deviations in refractive index other than the intended interaction of molecules, most notably the solvent contained in the sample passed over the sensing surface. Solvent correction adjusts reference-subtracted responses for small artefacts that can be introduced by variations in the bulk refractive index between samples. The correction is generally required when variations in the bulk refractive index are of the same order of magnitude as the response: this situation arises commonly in working with small organic biomolecules that give intrinsically low response values and that often require organic solvents such as dimethyl sulfoxide (DMSO) to maintain solubility.

The need for solvent correction arises because subtraction of the reference response does not exactly eliminate the contribution of the bulk solution to the measured response. Bulk solution is excluded from the volume occupied by ligand bound on the sensing surface, so that the bulk contribution to the response on the sensing surface is slightly smaller than that on the reference surface. As long as the refractive index of the samples is constant, this excluded volume effect introduces a constant error in reference subtraction which may be ignored for practical purposes. However, if the refractive index of the samples varies, the magnitude of the excluded volume effect will also vary. Especially for samples expected to give responses with low intensity, the bulk effect introduces a comparatively large error that cannot be ignored.

Reference measurements are therefore performed at regular intervals by passing solvent samples containing the solvent at different known concentrations over the sensing surface and creating reference-subtracted response values. These values are used for forming a calibration curve.

In order to perform the reference measurements, a dilution series is produced with a plurality of samples, each comprising a known concentration of the solvent. The process of making the dilution series is often performed by hand and is generally time consuming. It also takes up a large number of wells in the microwell plate used with the sensor system. There is always a risk of error or contamination that may affect the resulting calibration curve and thereby introduce errors in subsequent measurements.

It is important to note that other technical fields than the one described above also use dilution series and that the present invention as disclosed below could equally well be used within these.

Consequently, there is therefore a need for a more reliable, time efficient and cost efficient method for providing a dilution series.

SUMMARY OF THE INVENTION

The object of the invention is to provide new methods and a biosensor system for improving the evaluation of an interaction between an analyte in a fluid sample and a ligand immobilized on a sensing surface of a biosensor, which method and biosensor system overcomes one or more drawbacks of the prior art. This is achieved by the methods and system for preparing a dilution series according to the invention.

By using the method according to the first embodiment, dilution series can be prepared in an automated and time efficient way, requiring only two receptacles such as tubes or microwells. By using the method according to the second embodiment described further below, the concentration gradient in the injected sample allows for measurements on a continuously changing concentration and thereby gives the entire correction curve without having to rely on approximations around a number of data points.

Preferably, the dilution series are used for performing measurements that form a calibration curve, suitable for use with biosensor systems such as systems for surface plasmon resonance, but also suitable for use within other technical fields where calibration is required.

In the description below, the invention is described with regard to concentrations of an organic solvent such as DMSO, but it is to be noted especially that other substances may be used for other purposes than solvent correction. Such other substances include, but are not limited to, proteins, peptides, organic and inorganic compounds.

According to one aspect of the first embodiment of the method the second sample is mixed before injection in step e). Thereby, the concentration of the injected sample is the same in the entire sample and the risk for errors is decreased.

According to another aspect of the first embodiment of the method, the second concentration is zero. Thereby, a correction curve can be provided over a wide concentration interval, including very low concentrations.

According to one aspect of the second embodiment of the method, measurements are performed during a predetermined time that is the time that the injected combined sample passes through the measuring device. Thereby, response from the measurements can be performed continuously as the concentration changes from high to low or vice versa.

According to another aspect of the second method, the combined sample is created by adding the first sample onto the second sample so that a concentration gradient is formed in the combined sample, having the first concentration at an upper end of a receptacle and the second concentration at the lower end, and the injection is performed by injecting the combined sample from the bottom end of the receptacle. Thereby, since the combined sample results from the gradual mixing of the first sample and the second sample due to convection, the gradual mixing allows for a continuous change in concentration from the top to the bottom of the combined sample. By injecting the combined sample from the bottom, that continuous change is maintained in the injected sample and allow for measurements performed continuously from a lowest to a highest concentration, or from a highest to a lowest concentration.

The invention also provides a biosensor system arranged to perform the steps of the first method or the second method, as well as software for performing the method steps.

Many additional benefits and advantages of the invention will become readily apparent to the person skilled in the art in view of the detailed description below.

DRAWINGS

The invention will now be described in more detail with reference to the appended drawings, wherein FIG. 1 discloses a schematic side view of a biosensor system based on SPR;

FIG. 5 discloses three diagrams showing eight samples and their respective responses during injection, wherein 5A shows a prior art method of producing a dilution series, 5B shows the method according to the first preferred embodiment, and 5C shows the method according to the second preferred embodiment;

FIG. 6 discloses three diagrams 6A, 6B, 6C each showing one set of correction curves, wherein FIG. 6A discloses correction curves corresponding to the measurements of FIG. 5A, FIG. 6B discloses correction curves corresponding to the measurements of FIG. 5B, and FIG. 6C disclosing correction curves corresponding to the measurements of FIG. 5C; and FIG. 7 discloses four diagrams 7A, 7B, 7C and 7D, wherein

DETAILED DESCRIPTION

As mentioned above, the present invention relates to methods and biosensor systems for evaluation of an interaction between an analyte in a fluid sample and a ligand immobilized on a sensing surface of a biosensor.

Typically, the experimental binding data is obtained by sensor-based technology, which studies the molecular interactions and presents the results in real time as the interactions progress. Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Chemical sensors or biosensors are typically based on label-free techniques, detecting a change in a property of a sensing surface, such as e.g. mass, refractive index, or thickness for the immobilized layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers (e.g.

Bio-Layer Interferometry as implemented by ForteBio®), waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by GE Healthcare, which are based on surface plasmon resonance (SPR) and permit monitoring of surface binding interactions in real time between a ligand bound on a sensing surface and an analyte of interest. In this context, "ligand" is a molecule that has a known or unknown affinity for a given analyte and includes any capturing or catching agent immobilized on the surface, whereas "analyte" includes any specific binding partner thereto.

While in the detailed description, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip, which is contacted with the sample by a micro fluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
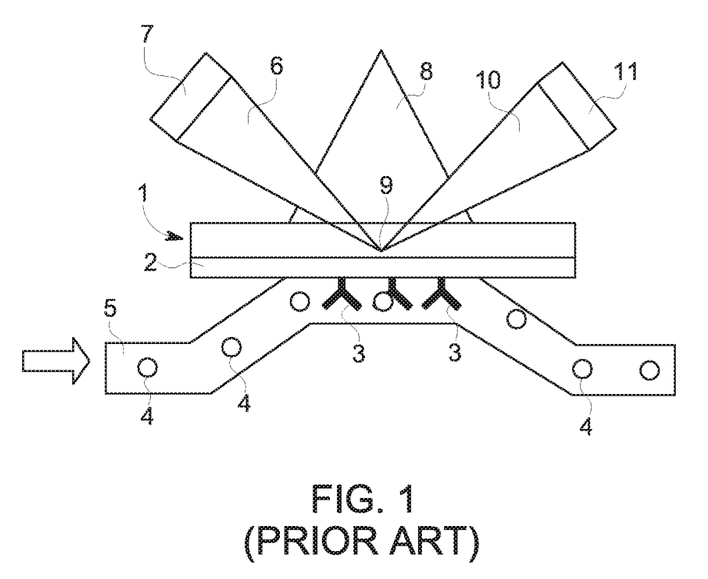

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436, 161. In addition, a detailed discussion of the technical aspects of the biosensor chips used in connection with the BIACORE® instruments may be found in U.S. Pat. No. 5,492,840.

Figure 2:
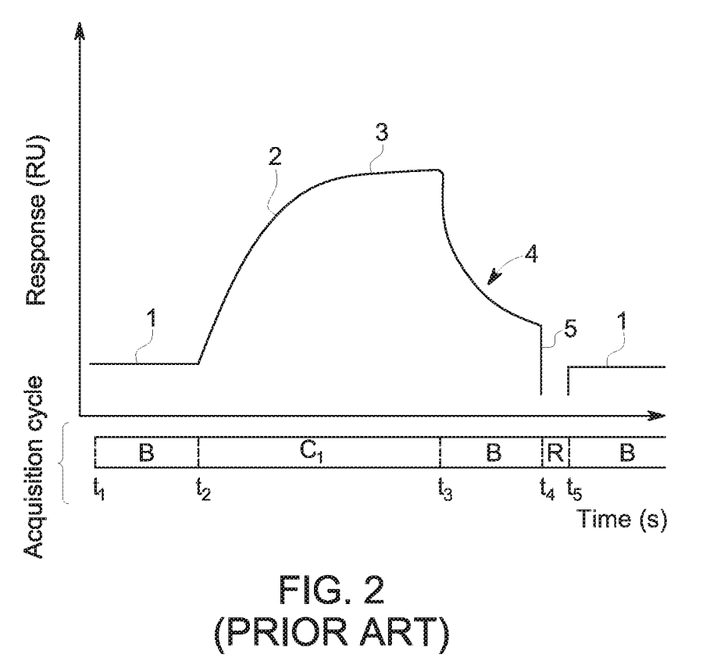
FIG. 2 discloses a representative sensorgram where the binding curve has visible association and dissociation phases.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or curve (binding isotherm), is usually called binding curve or sensorgram, also sometimes referred to in the art as "affinity trace" or "affmogram". In the BIACORE® system, the SPR response values are expressed in resonance units (RU). One RU represents a change of 0.0001° in the angle of minimum reflected light intensity, which for most proteins and other bio molecules correspond to a change in concentration of about 1 pg/mm^ on the sensing surface. As sample containing an analyte contacts the sensing surface, the capturing molecule (ligand) bound to the sensing surface interacts with the analyte in a step referred to as "association." This step is indicated in the binding curve by an increase in RU as the sample is initially brought into contact with the sensing surface. Conversely, "dissociation" normally occurs when the sample flow is replaced by, for example, a buffer flow. This step is indicated in the binding curve by a drop in RU over time as analyte dissociates from the surface-bound ligand. A representative binding curve (sensorgram) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Below the horizontal axis, the acquisition cycle for acquiring a binding curve is schematically disclosed divided in different time sections where the sensing surface is put into contact with different fluids. Initially, from to t2, buffer (B) is passed over the sensing surface giving the baseline response I in the binding curve. Then, during from t2 to t3, the sensing surface is contacted with a sample containing an analyte at a concentration Ci whereby an increase in signal is observed due to binding of the analyte. This part II of the binding curve is usually referred to as the "association phase". Eventually, a steady state condition is reached at or near the end of the association phase where the resonance signal plateaus at III (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of the association phase, at t3, the sample is often replaced with a continuous flow of buffer (B) and a decrease in signal reflects the dissociation, or release, of analyte from the surface. This part IV of the binding curve is usually referred to as the "dissociation phase". The analysis is optionally ended by a regeneration step, at t4, where a solution capable of removing bound analyte from the surface (R), while (ideally) maintaining the activity of the ligand, is injected over the sensing surface. This is indicated in part V of the sensorgram. At is injection of buffer (B) restores the baseline I and the surface is now ready for a new analysis. In some situations it may be convenient to omit the regeneration step V and initiate a new injection cycle without regeneration. Examples of such situations comprise concentration series of the same analyte, screening of analytes with a sufficiently high dissociation rate to allow essentially complete dissociation, etc. From the profiles of the association and dissociation phases II and IV, respectively, information regarding the binding and dissociation kinetics is obtained, and the height of the binding curve at III represents affinity (the response resulting from an interaction being related to the change in mass concentration on the surface).

Solvent correction (SC) is a procedure that corrects for sample-to-sample variations in bulk effects, which can introduce significant reference subtraction errors. These effects arise because reference and sensing surfaces are structurally different. Bulk solution is excluded from the volume occupied by ligand molecules immobilised on the sensing surface, effectively reducing potential bulk effects. Correction often becomes important for samples containing small molecules formulated and/or stored in organic solvents such as DMSO, which can dramatically affect the refractive index of the sample. The approach of SC is to measure the responses on both the sensing and reference surfaces during injections of blank samples containing a range of DMSO concentrations. Such runs are performed cyclically between each series of samples injected to correct for any drifts in the response. For each SC run, the reference-subtracted response on the sensing surface is then plotted against the reference response, and a quadratic polynomial is fit to the data, resulting in a correction curve disclosing the correction required due to bulk effects The present invention will now be described in detail with reference to FIG. 3-7. In this disclosure, the methods according to the invention are described using a biosensor system for performing measurements and registering responses that are used for solvent correction with a calibration curve, but it is important to note that the present methods could also be used with other systems as will be readily apparent to the person skilled in the art.

Figure 3A:
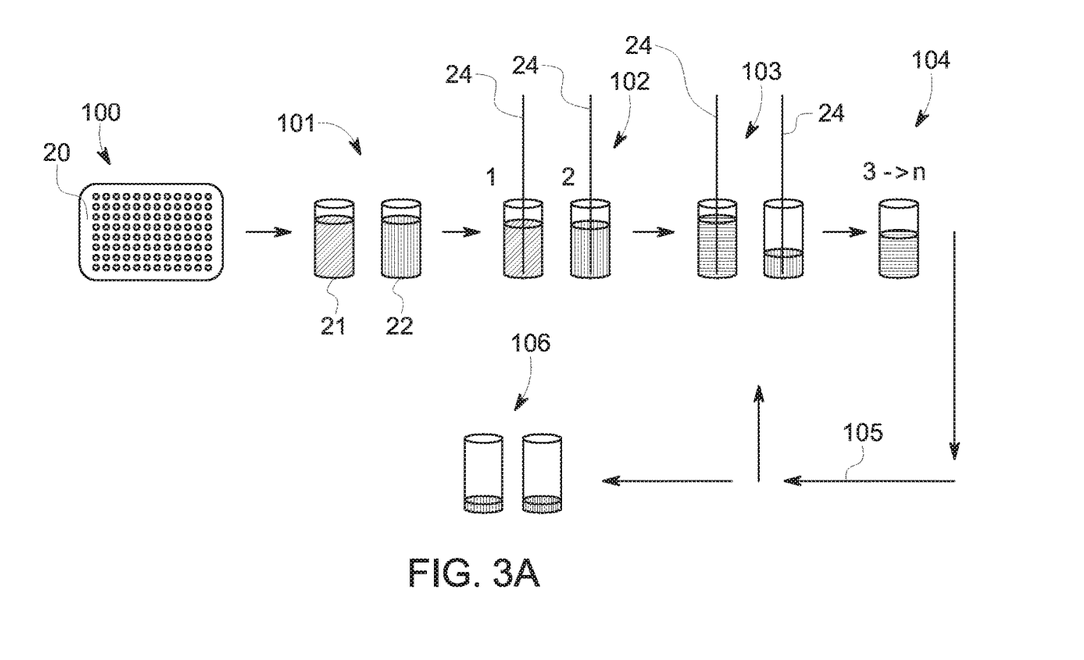
FIG. 3A discloses a schematic view of the steps of a first embodiment of the method according to a first embodiment of the present invention, in which mixing of the solution is performed in wells.

FIG. 3 discloses schematically the steps of a preferred embodiment of a first method for preparing a dilution series using receptacles such as tubes of a microwell plate in which samples of the dilution series are mixed.

As used herein, a sample is a quantity of fluid that may comprise a specific substance in a given concentration. The remaining fluid may be water or a suitable buffer, as is well known within the art.

In a preparation step 100, at least two tubes or a microwell with at least two empty wells are provided. In a first method step 101, a first sample 21 having a first concentration of a substance is provided in one well of the receptacles 20, and a second sample 22 having a second concentration of the same substance is provided in another well of the receptacles 20. The substance is preferably DMSO but may also be other organic solvents or another substance altogether. In the first sample 21, the concentration of the substance is relatively high, preferably 4-6% DMSO whereas the concentration of the substance in the second sample 22 is relatively low, preferably 1-3% DMSO. The concentration of the second sample may more preferably be very low or even zero. It is advantageous that the first and second concentrations are selected so that concentrations of future samples tested in a measuring device such as a biosensor system for surface plasmon resonance lie between the first and second concentrations, since this allows for calibration or correction of those samples with high accuracy.

In a second method step 102, a quantity of the first sample 21 and a quantity of the second sample 22 are injected, one at a time, into the measuring device. As each of the samples 21, 22 pass through a flow cell, at least one response is registered for each of the samples. The injection of the first and second samples 21, 22 can be made in any desired order. The quantity of the first and second sample is preferably selected to be sufficient for performing the measurement in the measuring device, and may therefore differ depending on the specific device or system used. In this embodiment, injections are performed by a needle 24 that is inserted into the receptacles 20, preferably one needle 24 for each of the two samples 21 and 22.

In another preferred embodiment, the first sample 21 is not injected into the measuring device, but rather only the second sample 22 is injected, at first having the second concentration and then having adjusted concentrations depending on the repeated addition of predetermined amounts of the first sample to form the dilution series. This does have the drawback of not providing a separate data point corresponding to the first concentration, but has the advantage of being a quicker and more convenient method when no future test samples having solvent concentrations equal to or nearly equal to the first concentration are to be tested.

In a third method step 103, a predetermined amount of the first sample 21 is added to the second sample 22, in which the concentration of sample 22 is altered. For example, the predetermined amount of the first sample 21 added may in one preferred embodiment be 80 µl, altering the concentration of the second sample 22 from 1.5% to 1.7% DMSO. Preferably, the second sample 22a is mixed to achieve a consistant, single concentration throughout.

In a fourth method step 104, a quantity of the second sample 22a having the altered concentration is injected into the biosensor system, and at least one response is registered.

In a fifth method step 105, the third and fourth steps 103, 104 are repeated to alter the concentration of the second sample 22 again and inject a quantity of the sample 22 to register a response for the altered concentration. This repetition goes on until a predetermined number of responses for a predetermined number of samples with different concentration have been registered.

In one embodiment, three or more responses are registered, resulting in three or more points in a subsequent calibration curve. This would mean to perform the third and fourth steps 103, 104 only once or more. More preferably, four or more preferably at least eight responses should be registered, meaning that the third and fourth steps 103, 104 are repeated once or five times, respectively. It is advantageous to have a higher number of responses, since this gives higher accuracy in a calibration curve, but it is still possible to achieve a basic calibration with reasonable accuracy using only three data points. Depending on the number of channels in the measuring device, four or eight data points may be especially suitable for the method of the present invention, due to the ease and convenience with which the current method can be achieved.

The dilution series are prepared in the biosensor system, thus allowing in-line sample preparation and measurement, which is particularly advantageous to high throughput applications including but not limited to drug screening. Thus, the dilution procedure can be automated and the needle 24 controlled by a the measuring device or by a separate device or control unit that serves to inject the samples 21, 22 into the measuring device and also perform the other steps of the method described above with regard to the first embodiment and below with regard to the second embodiment.

Figure 3B:
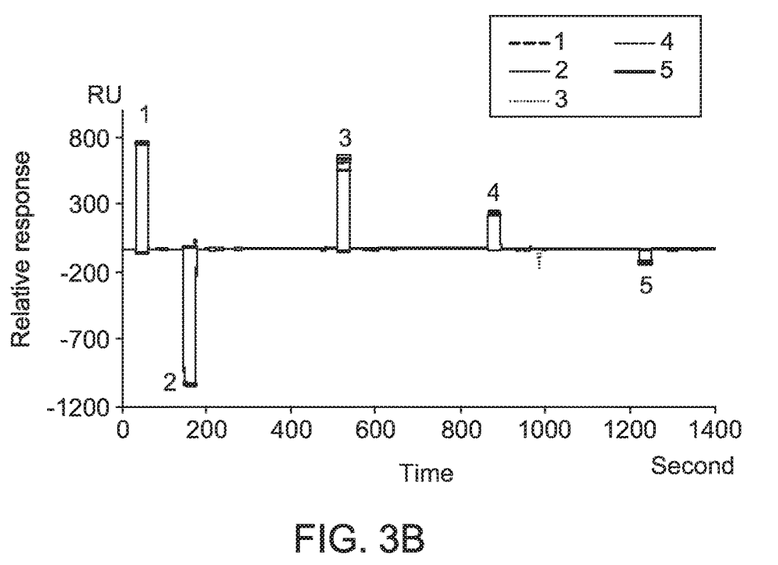
FIG. 3B discloses a diagram showing a relative response versus time for measurements performed on samples produced according to the first embodiment of the method disclosed in FIG. 3A.

Based on the registered responses, the sensorgram of FIG. 3B is formed in a sixth step 106, having five responses that correspond to five different concentrations injected into the measuring device. Thus, each of the samples 1-5 are injected at different times (shown by the x axis of FIG. 3B) and result in a relative response (shown by the y axis of FIG. 3B). Samples 1 and 2 have the first and second concentration, respectively, whereas the concentration of samples 3, 4 and 5 are given by the mixing of samples 1 and 2 as described above.

Figure 4A:
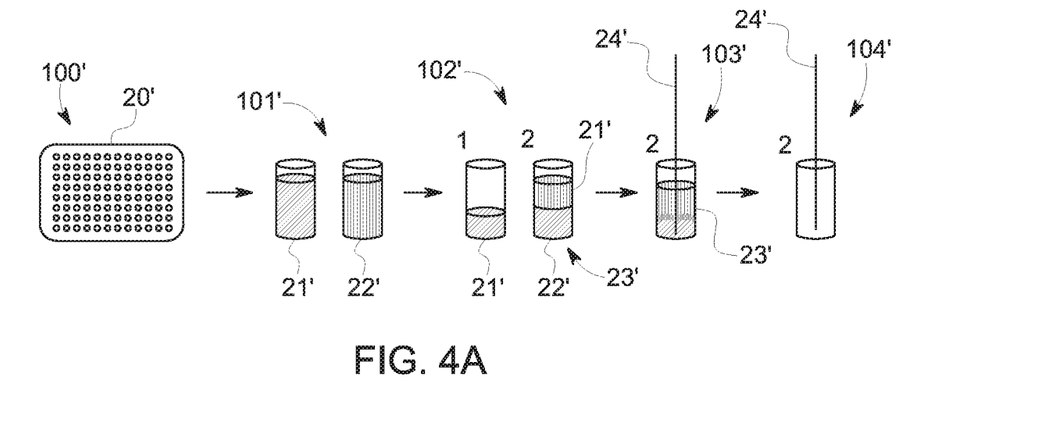
FIG. 4A discloses a schematic view of the steps of a second method according to a second preferred embodiment of the present invention, in which a convection mix is used.

FIG. 4 discloses schematically the steps of a preferred embodiment of a second method for preparing a dilution series using a convection mix in a receptacle for achieving a concentration gradient in a sample.

In a preparation step 100', receptacles 20' in the form of tubes or wells on a microwell plate are provided. In a first method step 101' a first sample 21' and a second sample 22' are each provided in a receptacle, wherein the first and second samples 21', 22' have different concentrations of a substance such as DMSO, similar to the first preferred embodiment described above. The concentration of the first sample 21' is relatively high whereas the concentration of the second sample 22' is relatively low, preferably very low or even zero. As an example, concentrations are for instance 4-6% DMSO in buffer in the first sample and 1-3% DMSO in buffer in the second sample.

In a second method step 102', the first sample 21' is added to the second sample 22' to form a combined sample 23', preferably without mixing so that a concentration gradient is formed ranging from the concentration of the first sample 21' (higher concentration) at a lower end of the combined sample 23' to the concentration of the second sample 22' (lower concentration) at an upper end of the combined sample 23'. The addition of the first sample 21' to the second sample 22' is preferably made by means of a needle 24' that injects the first sample 21' into the second sample 22'. In FIG. 4A, it was shown that the injected first sample 21' sits on the bottom of the second sample 22', however, in another embodiment, the injected first sample 21' may be at the top of the second sample 22'.

Figure 4B:
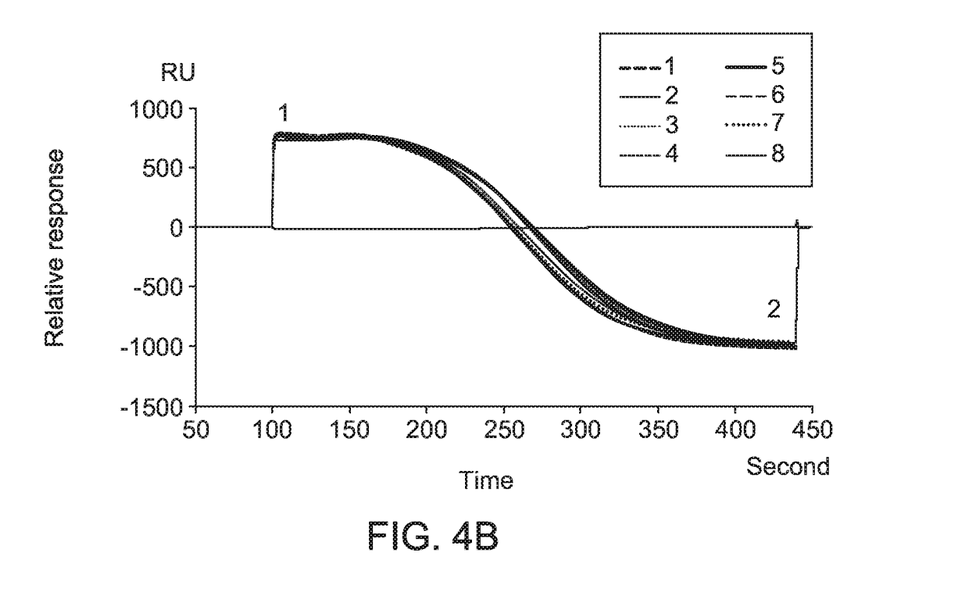
FIG. 4B discloses a diagram showing a relative response versus time for measurements performed on a combined sample produced according to the second embodiment of the method disclosed in FIG. 4A.

In a third method step 103', the combined sample 23' is injected into the biosensor system, starting with the lower end of the sample 22' having a lower concentration. Due to the concentration gradient resulting from the convection between the first sample 21' and the second sample 22', a continuous injection of a sample with a steadily increasing concentration is achieved, and measurements are performed during a predetermined time. Preferably, that predetermined time is the injection time during which the combined sample passes through the measuring device, so that measurements can be performed continuously during injection in order to provide a plurality of measurements that together form the sensorgram shown in FIG. 4. Due to the continuous measurements, responses are given for every small changes in concentration, for example, from the low to the high concentration or vice versa, and the resulting curve will therefore not require approximation around data points resulting from measurements at known concentrations but can provide accurate results for any given concentration between the first concentration and the second concentration.

Preferably, the injection is performed by a needle 24', and as an alternative the combined sample 23' may be injected starting from the top of the receptacle 20' rather than from the bottom.

After the third method step 103', the combined sample 23' has been removed from its receptacle 20', and in a fourth method step 104' a calibration curve is formed from the responses.

FIG. 4B discloses eight curves, each resulting from one injection of a combined sample according to the second embodiment of the method. Each injected sample has a concentration that changes continuously from the first concentration (denoted with a 1 in the diagram) to the second concentration (denoted with a 2 in the diagram), and it is to be noted that although the convection mixing may render each of the combined samples slightly different, the curves 1-8 are very similar. In the description above the sample with the higher concentration has been added to the sample with the lower concentration, but it is to be noted that the opposite is also possible and gives similar results in a similar way. With the injection from the bottom end of the combined sample 23', i.e. the sample having the second sample 22' at the bottom and the first sample 21' at the top, a continuous injection can be performed with precision and with a smooth change in concentration, giving reliable data and a suitable calibration curve for subsequent measurements in the biosensor system.

Figure 5A:
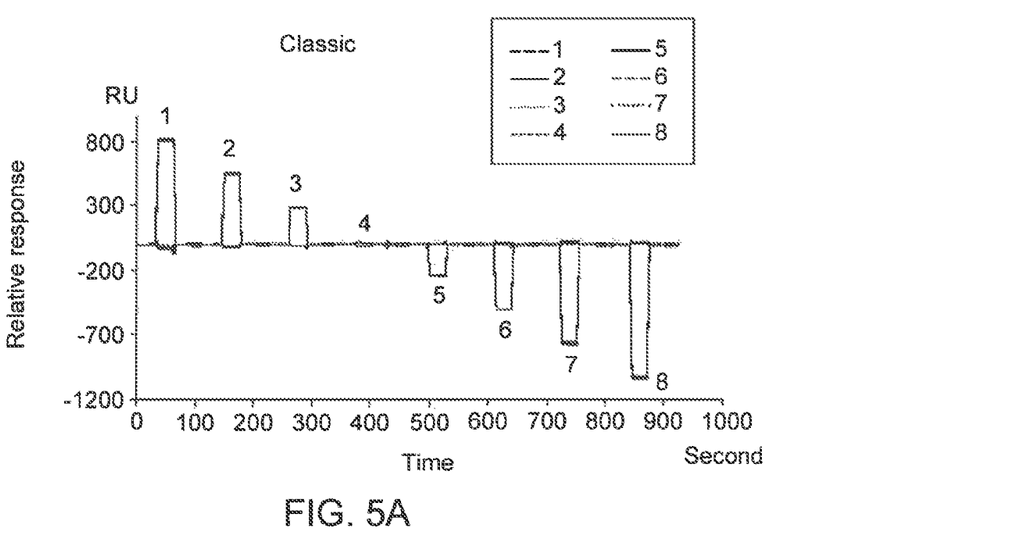
Figure 5B:
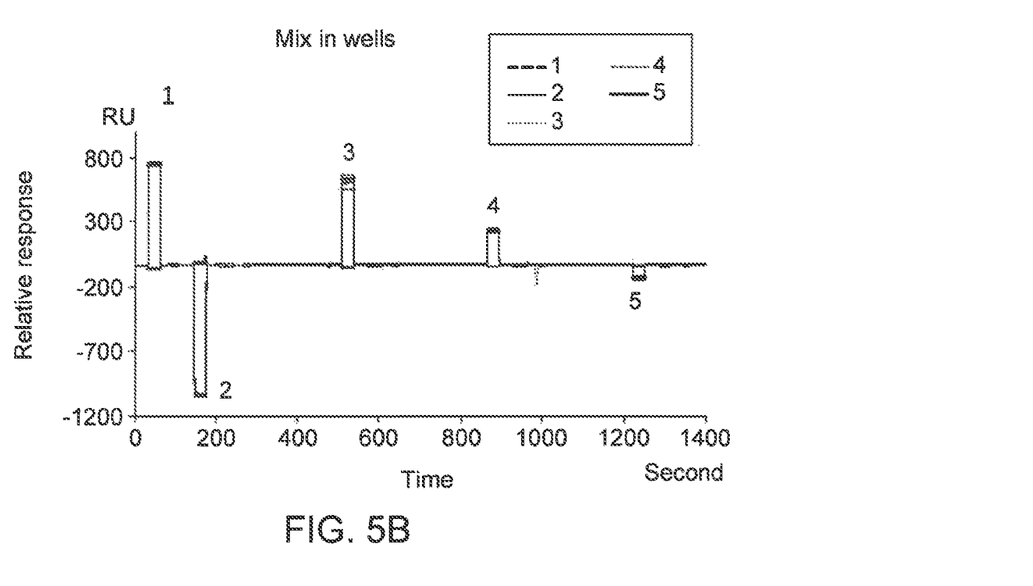
Figure 5C:
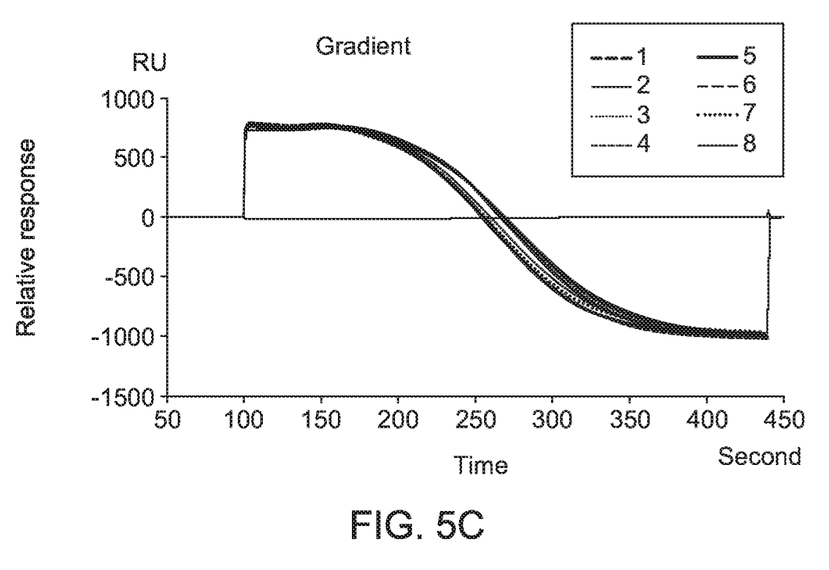

FIG. 5A-5C compares registered responses from three dilution series. In FIG. 5A (denoted "Classic"), a conventional method for preparing a dilution series has been used and the resulting samples injected one by one into the biosensor system starting with the highest concentration of the substance and progressing towards the lowest concentration. In FIG. 5B (denoted "Mix in wells"), the first embodiment of the method described above has been used, where the first and second samples injected are those with the highest and the lowest concentration. After them, samples with concentrations that progress from higher values towards lower are used, since each sample is produces through a combination of the second sample with a known quantity of the first sample. The third diagram (denoted "Gradient") discloses the second preferred embodiment of the method, where a combined sample has been injected starting with the highest concentration and progressing continuously towards the lowest concentration.

FIG. 5A discloses a diagram with eight samples (1-8) forming a dilution series that has been prepared according to a prior art method. In the diagram, a relative response for each of the samples versus injection time is disclosed.

FIG. 5B discloses a diagram with five samples (1-5) forming a dilution series that has been prepared according to the first embodiment of the method according to the present invention. In the diagram, a relative response for each of the five samples versus injection time is disclosed.

FIG. 5C discloses a diagram with eight graphs (1-8) each corresponding to an injection of a combined sample prepared according to the second embodiment of the present invention, wherein each injected sample has a concentration gradient that allows for the continuous variation of concentration from a first concentration (at a starting point for the graphs when injection begun) to a second concentration (at an end point for the graphs when injection is stopped). The graphs are very similar and are therefore not shown in greater detail.

Figure 6A:
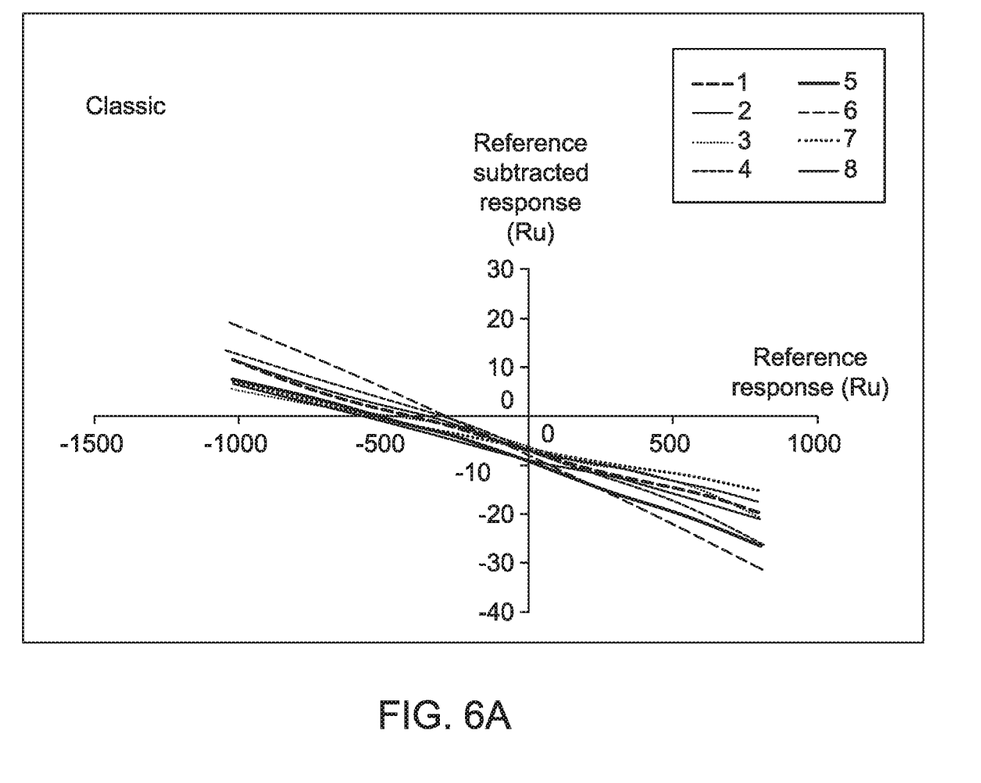
Figure 6B:
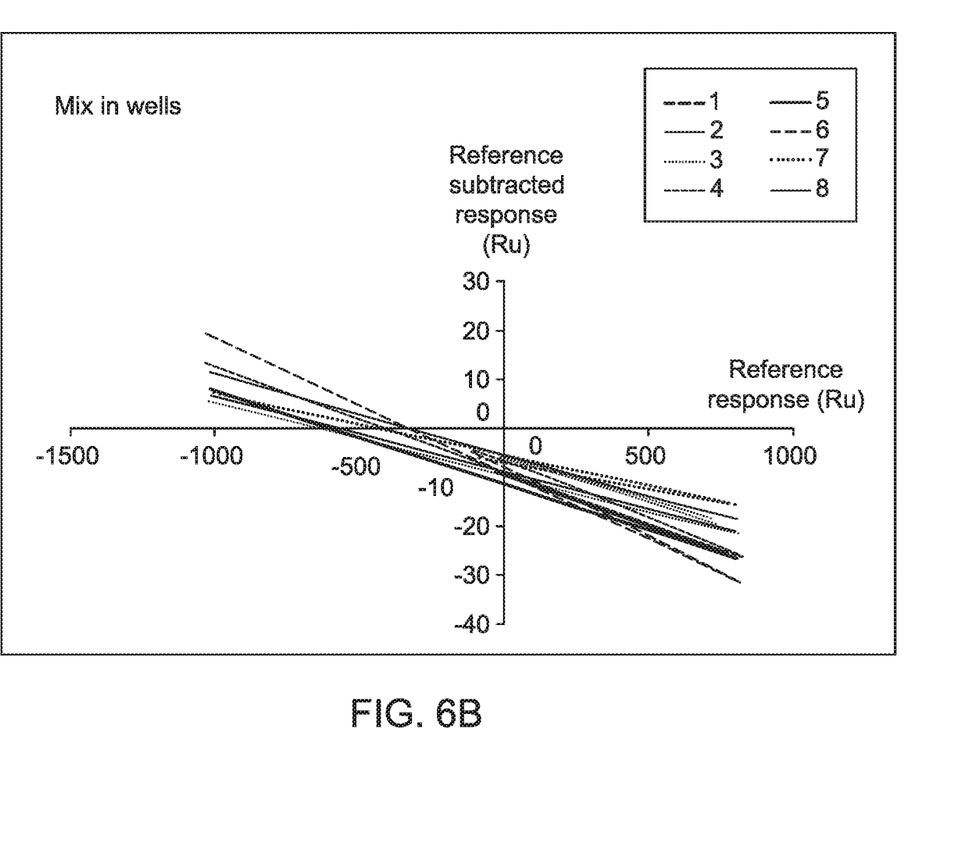
Figure 6C:
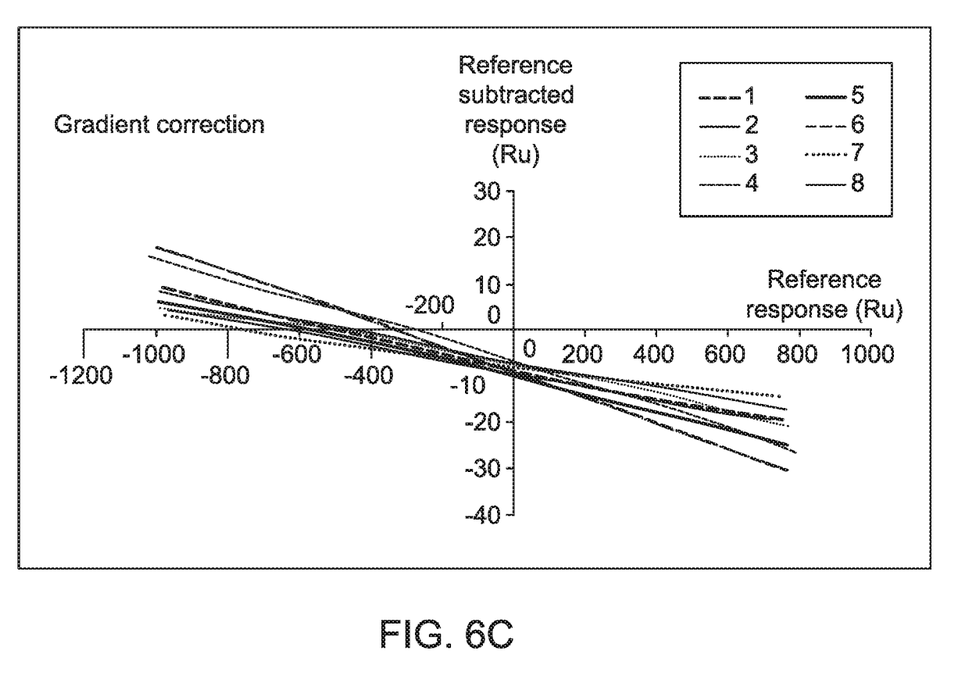

FIGS. 6A-6C represent correction curves resulting from the responses registered in each of the three diagrams in FIGS. 5A-5C, denoted in the same way as in that figure. As shown in FIGS. 6A-6C, regardless of the method used, similar correction curves are produced and can be used as solvent correction in subsequent measurements.

Thus, FIG. 6A discloses eight correction curves, each generated by using measurements performed on one dilution series (such as that shown in FIG. 5A) that has been produced through a prior art method. The correction curves are shown as reference subtracted response (in response units RU) versus reference response (in RU).

FIG. 6B discloses eight further correction curves, each generated by using measurements performed on one dilution series (such as that shown in FIG. 5B) that has been produced through the first embodiment of the present invention, and FIG. 6C discloses another set of eight correction curves that have been generated by using measurements performed on one combined sample produced according to the second embodiment of the invention.

Figure 7A:
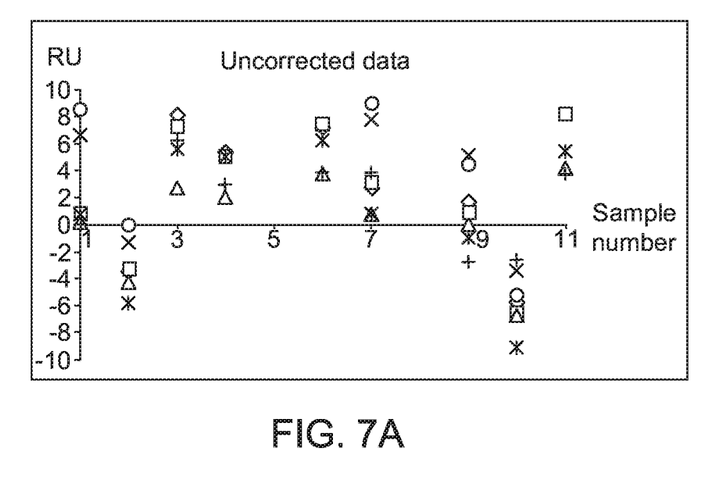
FIG. 7A, shows uncorrected data from measurements performed in a measuring device.
Figure 7B:
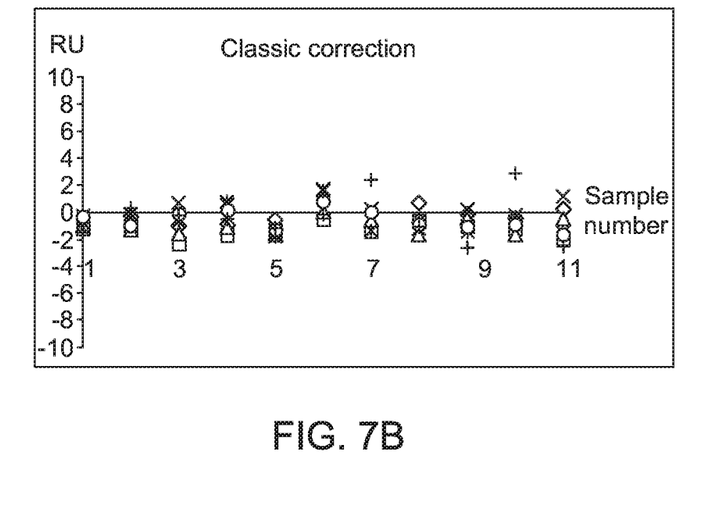
FIG. 7B shows the data of FIG. 7A corrected according to the correction curves of FIG. 6A.
Figure 7C:
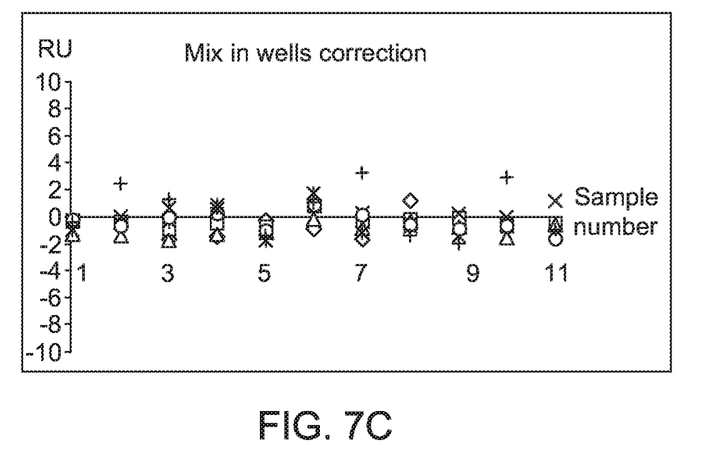
FIG. 7C shows the data of FIG. 7A corrected according to the correction curves of FIG. 6B.
Figure 7D:
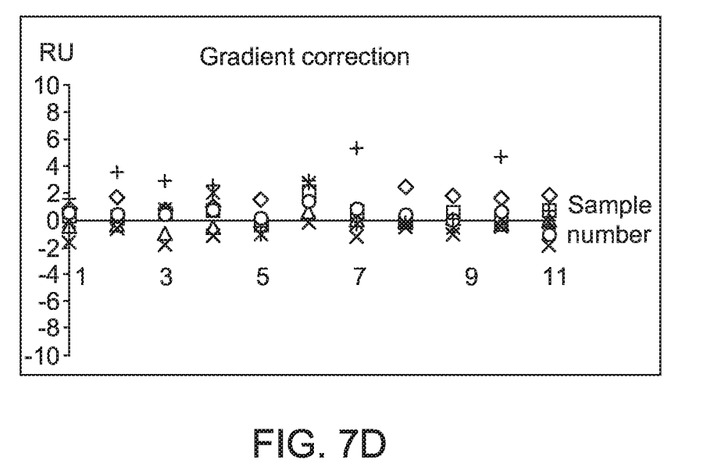
FIG. 7D shows the data of FIG. 7A corrected according to the correction curves of FIG. 6C.

FIGS. 7A-7D represent four diagrams where solvent correction is performed on a set of measurements performed in the biosensor system. Thus, FIG. 7A discloses data given by injecting any kind of samples into the biosensor system and measuring binding data at the sensing surface compared to a reference surface, FIG. 7B shows the data of FIG. 7A subjected to solvent correction using the correction curves of FIG. 6A (i.e. based on dilution series produced according to a prior art method). FIG. 7C shows the data of FIG. 7A subjected to solvent correction using the correction curves of FIG. 6B (i.e. based on dilution series produced according to the first embodiment of the method according to the present invention), and FIG. 7D shows the data of FIG. 7A subjected to solvent correction using the correction curves of FIG. 6C (i.e. based on the combined samples having concentration gradient and produced according to the second embodiment of the method).

Each of the methods for solvent correction produce satisfactory results in correcting the data of FIG. 7A, but the method according to the invention for producing the dilution series or the combined sample with the concentration gradient have clear benefits compared to the prior art methods in being time efficient and reliable while also requiring a significantly lower number of wells on a microwell plate. In addition, the methods according to the invention allow the automated in-line sample preparation of the dilution series in the biosensor system, thus providing significant improvement to the sample preparation and measurement high throughput capability to the biosensor system.

The invention further comprises a biosensor system arranged to perform the steps of at least one of the methods described herein. The biosensor system is preferably a system for performing surface plasmon resonance, but could also be another biosensor system where dilution series are required to provide calibration.

Also provided is a data processing apparatus comprising means for carrying out the steps of at least one of the methods. Preferably, the data processing apparatus is integrated with a control unit of the biosensor system but it could also be a stand-alone system that communicates with the control unit of the biosensor system or with another measurement device capable of performing the measurements on the samples. A computer program product is also provided, having software that can be executed by the data processing apparatus, along with a computer-readable storage medium for storing the computer program product. The storage medium can be a memory device of a computer or similar, but can also be a memory stick or disc able to hold software, or another suitable storage medium as is well known to the person skilled in the art.

The features of the various embodiments described above may be freely combined with each other within the scope of the present invention, except where such a combination would be unsuitable as will be readily apparent to the person skilled in the art.

The invention claimed is:

1. A method for preparing a dilution series in a biosensor system, comprising:
   a) providing a first sample having a first concentration of a substance and a second sample having a second concentration of said substance,
   b) injecting a quantity of the second sample to a measuring device and registering at least one response from a measurement,
   c) altering the concentration of the second sample by adding an amount of the first sample to the second sample,
   d) injecting a quantity of the second sample generated in step (c) to the measuring device and registering at least one response from a measurement,
   e) repeating steps c) and d) until a predetermined number of responses have been registered, said predetermined number of responses being at least three.

2. The method according to claim 1, wherein the registered responses are used to form a calibration curve.

3. The method according to claim 1, wherein the predetermined number of responses being at least four.

4. The method Method according to claim 1, wherein the second concentration is zero.

5. The method according to claim 1, wherein the substance comprises an organic solvent.

6. The method according to claim 1, further comprising:
   f) Injecting a quantity of the first sample to the measuring device and registering at least one response from a measurement.

7. The method according to claim 2, wherein the calibration curve is used for surface plasmon resonance.

8. The method of claim 1, wherein the predetermined number of responses being at least four.

9. The method of claim 5, wherein the organic solvent is DMSO (dimethyl sulfoxide).

\* \* \* \* \*